US012588897B2

(12) United States Patent
Li

(10) Patent No.: US 12,588,897 B2
(45) Date of Patent: Mar. 31, 2026

(54) VISCOELASTICITY MEASUREMENT METHOD AND ULTRASONIC IMAGING SYSTEM

(71) Applicant: SHENZHEN MINDRAY BIO-MEDICAL ELECTRONICS CO., LTD., Guangdong (CN)

(72) Inventor: Shuangshuang Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 91 days.

(21) Appl. No.: 18/217,385

(22) Filed: Jun. 30, 2023

(65) Prior Publication Data

US 2024/0156438 A1     May 16, 2024

Related U.S. Application Data

(63) Continuation of application No. PCT/CN2021/070144, filed on Jan. 4, 2021.

(51) Int. Cl.
*A61B 8/00* (2006.01)

(52) U.S. Cl.
CPC .............. *A61B 8/485* (2013.01); *A61B 8/463* (2013.01)

(58) Field of Classification Search
None
See application file for complete search history.

(56) References Cited

U.S. PATENT DOCUMENTS

| | | | |
|---|---|---|---|
| 8,469,891 | B2 | 6/2013 | Maleke et al. |
| 9,895,137 | B2 | 2/2018 | Tabaru et al. |
| 10,376,242 | B2 | 8/2019 | Labyed et al. |
| 11,154,277 | B2 | 10/2021 | Rosenzweig |

(Continued)

FOREIGN PATENT DOCUMENTS

| | | |
|---|---|---|
| CN | 102641137 A | 8/2012 |
| CN | 103054552 A | 4/2013 |

(Continued)

OTHER PUBLICATIONS

PCT International Search Report and the Written Opinion mailed Oct. 13, 2021, issued in related International Application No. PCT/CN2021/070144, with partial English translation (13 pages).

(Continued)

*Primary Examiner* — Jonathan Cwern
(74) *Attorney, Agent, or Firm* — Sheppard Mullin Richter & Hampton LLP

(57) ABSTRACT

A viscoelasticity measurement method and an ultrasonic imaging system. The method includes: generating a shear wave that propagates in a target area of a measured object (S210); emitting, to the target area, an ultrasonic wave that tracks the shear wave, and receiving an ultrasonic echo returned from the target area, so as to obtain ultrasonic echo data (S220); obtaining tissue motion information in a shear wave propagation process according to the ultrasonic echo data (S230); extracting, from the tissue motion information, parts of tissue motion information corresponding to shear waves of at least two different frequencies (S240); and outputting the parts of tissue motion information of the shear waves of the at least two different frequencies. The parts of tissue motion information are used for reflecting a viscosity feature of the target area (S250).

17 Claims, 9 Drawing Sheets

(56) References Cited

U.S. PATENT DOCUMENTS

| | | | |
|---|---|---|---|
| 11,529,121 | B2 | 12/2022 | Sandrin et al. |
| 2015/0133783 | A1 | 5/2015 | Tabaru et al. |
| 2015/0148673 | A1 | 5/2015 | Yoshikawa et al. |
| 2016/0143625 | A1 | 5/2016 | Shikata |
| 2017/0311929 | A1* | 11/2017 | Shao ........................ A61B 8/54 |
| 2020/0410667 | A1* | 12/2020 | Ormachea Quispe ....................... A61B 8/5207 |
| 2021/0059643 | A1* | 3/2021 | Liu .................... G01S 7/52085 |

FOREIGN PATENT DOCUMENTS

| | | |
|---|---|---|
| CN | 104302233 A | 1/2015 |
| CN | 104380134 A | 2/2015 |
| CN | 104622502 A | 5/2015 |
| CN | 204562216 U | 8/2015 |
| CN | 105615921 A | 6/2016 |
| CN | 106037796 A | 10/2016 |
| CN | 106037816 A | 10/2016 |
| CN | 106175831 A | 12/2016 |
| CN | 106963419 A | 7/2017 |
| CN | 108451499 A | 8/2018 |
| CN | 109717899 A | 5/2019 |
| CN | 110368030 A | 10/2019 |
| WO | 2011/012340 A1 | 2/2011 |
| WO | 2014/128593 A1 | 8/2014 |
| WO | 2018/224602 A1 | 12/2018 |

OTHER PUBLICATIONS

PCT International Preliminary Report on Patentability mailed Jul. 13, 2023, issued in related International Application No. PCT/CN2021/070144, with English translation (10 pages).

* cited by examiner

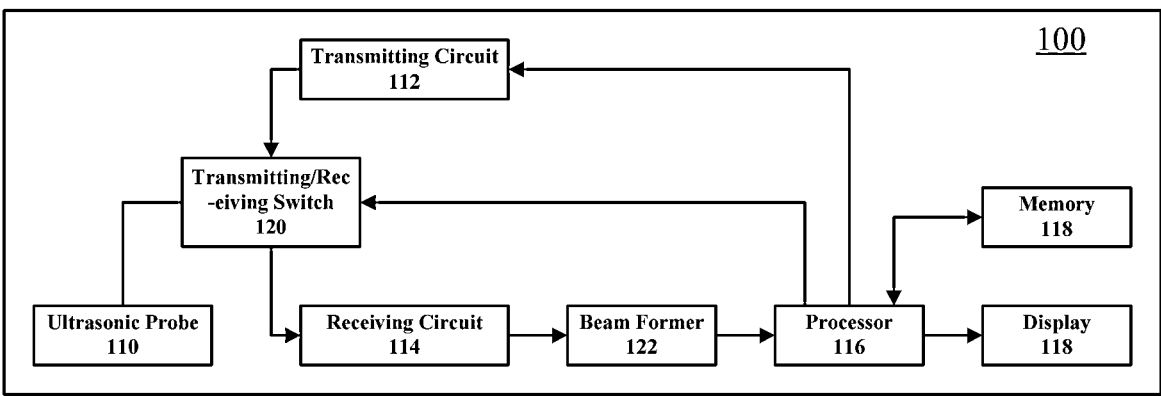

Generate shear waves propagating in a target area of an object to be examined

Transmit ultrasonic waves for tracking the shear waves to the target area, and receive ultrasonic echoes returned from the target area to obtain ultrasonic echo data Obtain the tissue motion information in the propagation of the shear waves according to the ultrasonic echo data Obtain the target tissue motion information corresponding to at least two shear waves of different frequencies from the tissue motion information Output the target tissue motion information corresponding to the at least two shear waves of different frequencies, where the target tissue motion information represents a viscosity characteristics of the target area

S710 | Generate at least two shear waves of different frequencies sequentially in the target area of the object to be examined S720 | Transmit ultrasonic waves for tracking the at least two shear waves of different frequencies to the target area, and receive ultrasonic echoes returned from the target area to obtain ultrasonic echo data S730 | Obtain the target tissue motion information corresponding to the at least two shear waves of different frequencies according to the ultrasonic echo data S740 | Output the target tissue motion information corresponding to the at least two shear waves of different frequencies, where the target tissue motion information represents t h e viscosity characteristics of the target area

FIG. 7

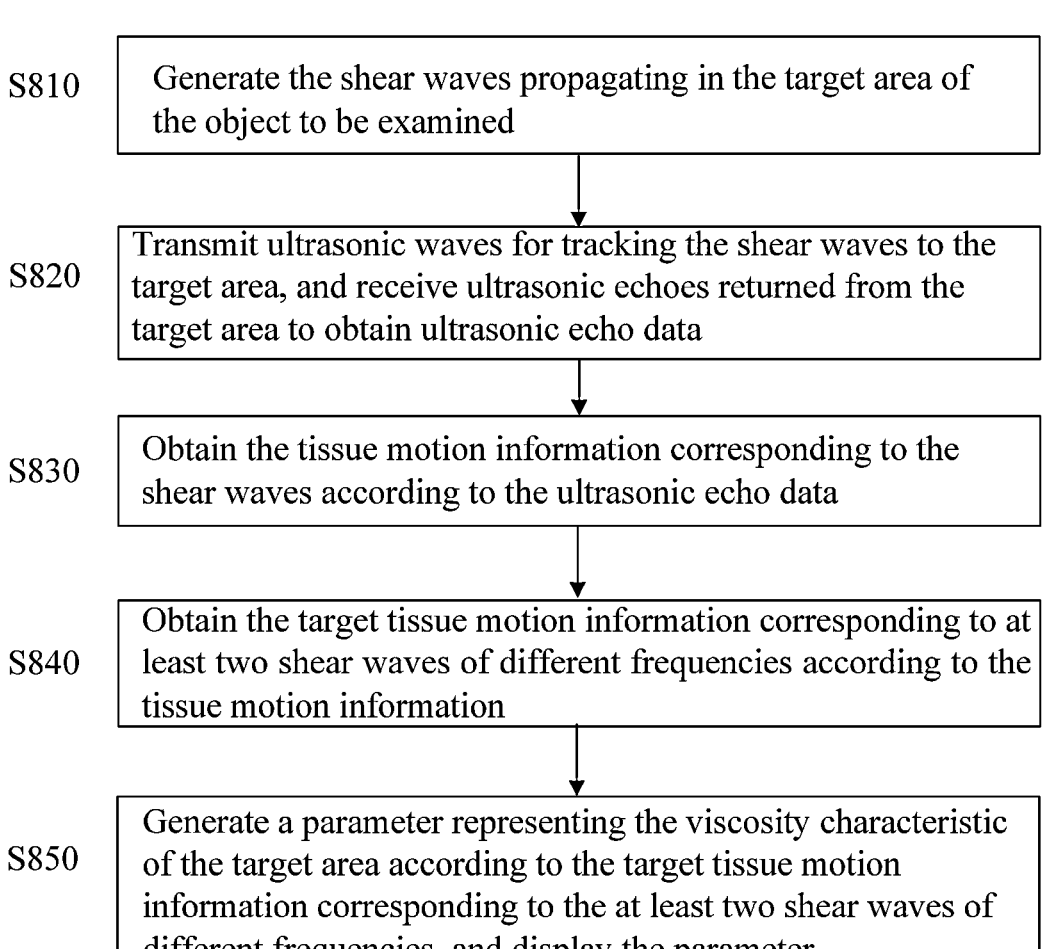

800

S810 | Generate the shear waves propagating in the target area of the object to be examined S820 | Transmit ultrasonic waves for tracking the shear waves to the target area, and receive ultrasonic echoes returned from the target area to obtain ultrasonic echo data S830 | Obtain the tissue motion information corresponding to the shear waves according to the ultrasonic echo data S840 | Obtain the target tissue motion information corresponding to at least two shear waves of different frequencies according to the tissue motion information S850 | Generate a parameter representing the viscosity characteristic of the target area according to the target tissue motion information corresponding to the at least two shear waves of different frequencies, and display the parameter

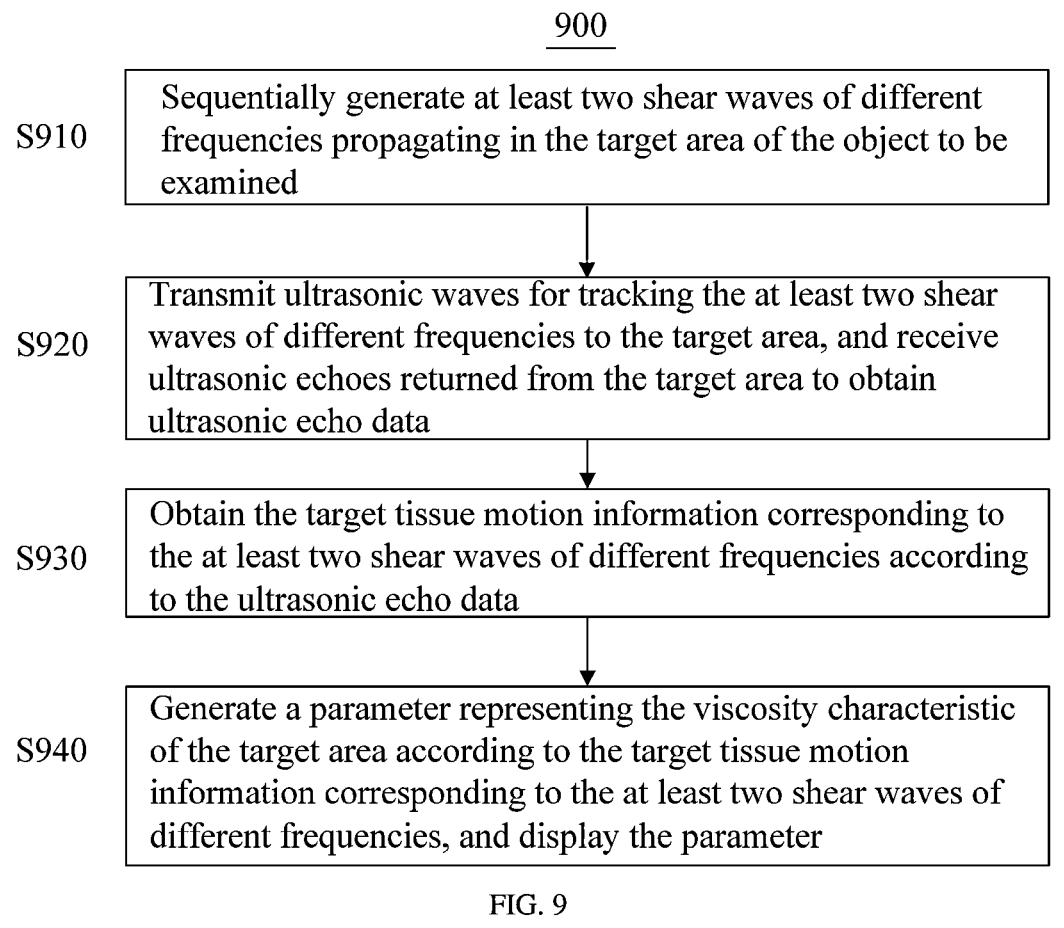

| S910 | Sequentially generate at least two shear waves of different frequencies propagating in the target area of the object to be examined |

| S920 | Transmit ultrasonic waves for tracking the at least two shear waves of different frequencies to the target area, and receive ultrasonic echoes returned from the target area to obtain ultrasonic echo data |

| S930 | Obtain the target tissue motion information corresponding to the at least two shear waves of different frequencies according to the ultrasonic echo data |

| S940 | Generate a parameter representing the viscosity characteristic of the target area according to the target tissue motion information corresponding to the at least two shear waves of different frequencies, and display the parameter |

FIG. 9

VISCOELASTICITY MEASUREMENT METHOD AND ULTRASONIC IMAGING SYSTEM

CROSS-REFERENCE TO RELATED APPLICATION

The application is a continuation application of International Patent Application No. PCT/CN2021/070144, filed with the China National Intellectual Property Administration (CNIPA) on Jan. 4, 2021. The entire content of all of the above-identified applications is incorporated herein by reference.

TECHNICAL FIELD

The present disclosure relates to ultrasonic imaging, more particularly to viscoelasticity measurement methods and ultrasonic imaging system thereof.

BACKGROUND

In ultrasonic elastography technology, hardness-related information of tissue is extracted for imaging, which is related to the non-invasive auxiliary diagnosis of major diseases such as breast cancer or liver cirrhosis, etc. Therefore, it has been a research hotspot in the field of ultrasonic imaging in the past two decades. After years of development, ultrasonic elastography technology has gradually matured, and in recent years, has been more widely used in clinical research and auxiliary diagnosis of liver, breast, thyroid, musculoskeletal, vascular, prostate, cervix or other parts of human body. By the ultrasonic elastography technology, the difference between the hardness of the lesion relative to the surrounding tissue can be qualitatively presented, or the physical parameters related to the hardness of the target tissue, such as Young's modulus or shear modulus, etc., can be quantitatively presented. Therefore, it is widely welcomed by doctors.

Commonly, the ultrasonic elastography technology includes strain elastography, shear wave elastography and instantaneous elastography, etc. With the shear wave elastography technology, special pulses are transmitted into the tissue. The acoustic radiation force generated thereby can lead to the propagation of shear waves in the tissue. The propagation process of the shear waves can be detected and recorded with ultrasonic waves, and the propagation velocity of the shear waves can be calculated. Finally, the elastic modulus representing the tissue hardness can be obtained, thereby realizing quantitative elastography. This technology greatly expands the clinical application field of elastography and arouses great research interest.

More and more studies have shown that human tissue has viscosity property in addition to the elasticity property, and the elasticity and viscosity together affect the propagation velocity of the shear waves in the tissue. However, in most current elasticity-related studies, the tissue is regarded as a pure elastomer, and the imaging of the elastography techniques are mainly based on the assumption of pure elastomer. In particular, in the quantitative elastography techniques, usually only the elastic modulus is calculated for display.

SUMMARY

A series of concepts in simplified forms are introduced in the SUMMARY section, which will be described in further detail in the DETAILED DESCRIPTION section. The SUMMARY part of the present disclosure is not intent to define the key features and necessary technical features of the claimed technical solutions, much less to determine the protection scope of the claimed technical solutions.

The first aspect of the embodiments of the present disclosure provides a viscoelasticity measurement method, which includes:

generating shear waves propagating in a target area of an object to be examined;

transmitting ultrasonic waves for tracking the shear waves to the target area, and receiving ultrasonic echoes returned from the target area to obtain an ultrasonic echo data;

obtaining a tissue motion information in the propagation of the shear waves according to the ultrasonic echo data;

obtaining tissue motion target information corresponding to at least two shear waves of different frequencies from the tissue motion information; and outputting the tissue motion target information corresponding to the at least two shear waves of different frequencies, wherein the tissue motion target information represents a viscosity characteristic of the target area.

The second aspect of the embodiments of the present disclosure provides a viscoelasticity measurement method, which includes:

generating at least two shear waves of different frequencies sequentially in a target area of an object to be examined;

transmitting ultrasonic waves for tracking the at least two shear waves of different frequencies to the target area, and receiving ultrasonic echoes returned from the target area to obtain ultrasonic echo data;

obtaining tissue motion target information corresponding to the at least two shear waves of different frequencies according to the ultrasonic echo data; and outputting the tissue motion target information corresponding to the at least two shear waves of different frequencies, wherein the tissue motion target information represents a viscosity characteristic of the target area.

The third aspect of the embodiments of the present disclosure provides a viscoelasticity measurement method, which includes:

generating shear waves propagating in a target area of an object to be examined;

transmitting ultrasonic waves for tracking the shear waves to the target area, and receiving ultrasonic echoes returned from the target area to obtain ultrasonic echo data;

obtaining a tissue motion information corresponding to the shear waves according to the ultrasonic echo data;

obtaining tissue motion target information corresponding to at least two shear waves of different frequencies according to the tissue motion information; and generating a parameter representing a viscosity characteristic of the target area according to the tissue motion target information corresponding to the at least two shear waves of different frequencies, and displaying the parameter.

The fourth aspect of the embodiments of the present disclosure provides a viscoelasticity measurement method, which includes:

sequentially generating at least two shear waves of different frequencies propagating in a target area of an object to be examined;

transmitting ultrasonic waves for tracking the at least two shear waves of different frequencies to the target area, and receiving ultrasonic echoes returned from the target area to obtain ultrasonic echo data;

obtaining tissue motion target information corresponding to the at least two shear waves of different frequencies according to the ultrasonic echo data; and generating a parameter representing a viscosity characteristic of the target area according to the tissue motion target information corresponding to the at least two shear waves of different frequencies, and displaying the parameter.

The fifth aspect of the embodiments of the present disclosure provides a viscoelasticity measurement method, which includes:

generating a shear wave with a target frequency propagating in a target area of an object to be examined;

transmitting ultrasonic waves for tracking the shear wave with the target frequency to the target area, and receiving ultrasonic echoes returned from the target area to obtain ultrasonic echo data;

obtaining a tissue motion information corresponding to the shear wave with the target frequency according to the ultrasonic echo data; and outputting the tissue motion information corresponding to the shear wave with the target frequency, wherein the tissue motion information represents a viscosity characteristic of the target area.

The sixth aspect of the embodiments of the present disclosure provides an ultrasonic imaging system, which includes:

an ultrasonic probe configured to generate shear waves propagating in a target area of an object to be examined;

a transmitting circuit configured to excite the ultrasonic probe to transmit ultrasonic waves for tracking the shear waves to the target area;

a receiving circuit configured to control the ultrasonic probe to receive ultrasonic echoes returned from the target area to obtain ultrasonic echo data; and a processor configured to perform the viscoelasticity measurement method of the first aspect of the present disclosure.

The seventh aspect of the embodiments of the present disclosure provides an ultrasonic imaging system, which includes:

an ultrasonic probe configured to sequentially generate at least two shear waves of different frequencies propagating in a target area of an object to be examined;

a transmitting circuit configured to excite the ultrasonic probe to transmit ultrasonic waves for tracking the at least two shear waves of different frequencies to the target area;

a receiving circuit configured to control the ultrasonic probe to receive ultrasonic echoes returned from the target area to obtain ultrasonic echo data; and a processor configured to perform the viscoelasticity measurement method of the second aspect of the present disclosure.

The eighth aspect of the embodiments of the present disclosure provides an ultrasonic imaging system, which includes:

an ultrasonic probe configured to generate shear waves propagating in a target area of an object to be examined;

a transmitting circuit configured to excite the ultrasonic probe to transmit ultrasonic waves for tracking the shear waves to the target area;

a receiving circuit configured to control the ultrasonic probe to receive ultrasonic echoes returned from the target area to obtain ultrasonic echo data; and a processor configured to perform the viscoelasticity measurement method of the third aspect of the present disclosure.

The ninth aspect of the embodiments of the present disclosure provides an ultrasonic imaging system, which includes:

an ultrasonic probe configured to sequentially generate at least two shear waves of different frequencies propagating in a target area of an object to be examined;

a transmitting circuit configured to excite the ultrasonic probe to transmit ultrasonic waves for tracking the at least two shear waves of different frequencies to the target area;

a receiving circuit configured to control the ultrasonic probe to receive ultrasonic echoes returned from the target area to obtain ultrasonic echo data; and a processor configured to perform the viscoelasticity measurement method of the fourth aspect of the present disclosure.

The tenth aspect of the embodiments of the present disclosure provides an ultrasonic imaging system, which includes:

an ultrasonic probe configured to generate a shear wave of target frequency propagating in a target area of an object to be examined;

a transmitting circuit configured to excite the ultrasonic probe to transmit ultrasonic waves for tracking the shear wave to the target area;

a receiving circuit configured to control the ultrasonic probe to receive ultrasonic echoes returned from the target area to obtain ultrasonic echo data; and a processor configured to perform the viscoelasticity measurement method of the fifth aspect of the present disclosure.

The viscoelasticity measurement methods and the ultrasonic imaging systems of the embodiments of the present disclosure represent the viscosity characteristics of the tissue through the tissue motion target information of at least two shear waves of different frequencies.

BRIEF DESCRIPTION OF THE DRAWINGS

FIG. 1 shows a schematic block diagram of an ultrasonic imaging system according to an embodiment of the present disclosure;

FIG. 2 is a schematic flowchart of a viscoelasticity measurement method according to an embodiment of the present disclosure;

FIG. 7 is a schematic flowchart of a viscoelasticity measurement method according to another embodiment of the present disclosure;

FIG. 8 is a schematic flowchart of a viscoelasticity measurement method according to another embodiment of the present disclosure;

FIG. 9 is a schematic flowchart of a viscoelasticity measurement method according to another embodiment of the present disclosure.

DETAILED DESCRIPTION

Figure 3:
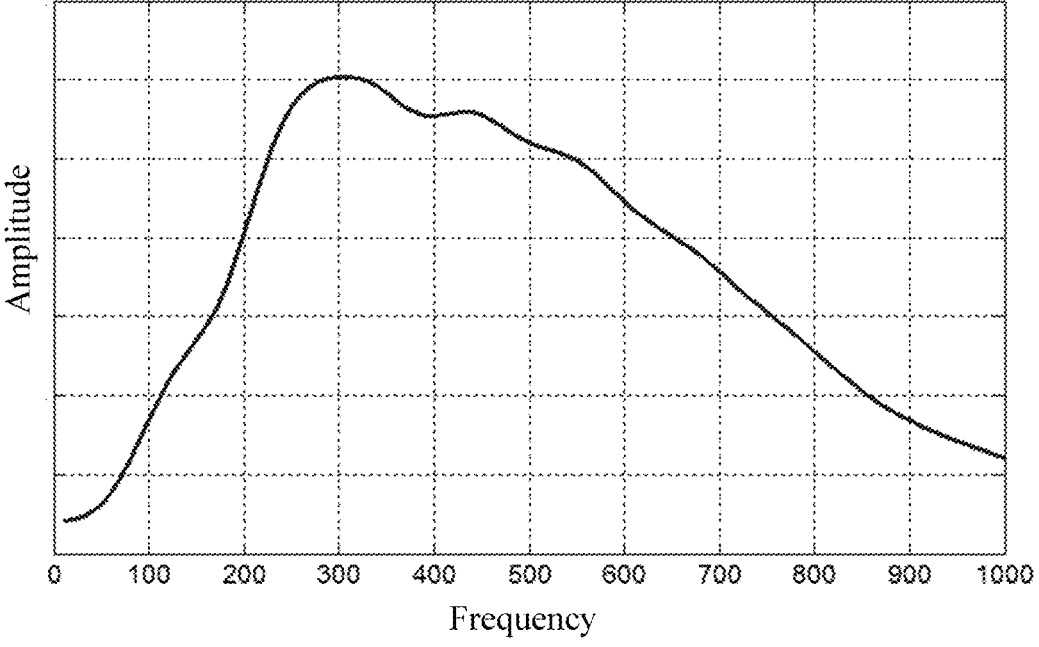
FIG. 3 is a spectrogram of tissue motion information according to an embodiment of the present disclosure.

In order to make the objectives, technical solutions and advantages of the present disclosure clearer, embodiments of the present disclosure will be described in detail below with reference to the drawings. However, the described embodiments are only a part, but not all, of the embodiments of the present disclosure. It should be understood that the present disclosure is not limited by the embodiments described herein. All other embodiments obtained by those skilled in the art based on the described embodiments without creative effort should fall within the protection scope of the present disclosure.

In the following description, numerous specific details are given in order to provide a more thorough understanding to the present disclosure. However, it will be apparent to those skilled in the art that the present disclosure may be implemented without one or more of these details. In other examples, some technical features known in the art will not be described in order to avoid confusion with the present disclosure.

It should be understood that the present disclosure can be embodied in different forms and should not be construed as being limited to the embodiments set forth herein. On the contrary, the provision of these embodiments will enable the disclosure to be thorough and complete, and fully convey the scope of the present disclosure to those skilled in the art.

The terms used herein are for the purpose of describing specific embodiments only, but not intended to limit the present disclosure. As used herein, the singular forms "a", "an" and "the/said" are also intended to include the plural forms unless the context clearly dictates otherwise. It should also be understood that the terms "consisting of" and/or "including", when used herein, determine the presence of said features, integers, steps, operations, elements and/or components, but not exclude the presence or addition of one or more other features, integers, steps, operations, elements, components and/or groups. As used herein, the term "and/or" includes any and all combinations of the listed items.

In order to thoroughly understand the present disclosure, detailed steps and detailed structures will be described in the following description in order to explain the technical solutions proposed by the present disclosure. The embodiments of the present disclosure will be described in detail as follows. However, in addition to the detailed description, the present disclosure may have other implementations.

In order to thoroughly understand the present disclosure, detailed structures will be described in the following description in order to explain the technical solutions proposed by the present disclosure. The embodiments of the present disclosure will be described in detail as follows.

However, in addition to the detailed description, the present disclosure may also have other implementations.

An ultrasonic imaging system according to an embodiment of the present disclosure will be described with reference to FIG. 1, which shows a schematic structural block diagram of an ultrasonic imaging system 100 according to an embodiment of the present disclosure.

As shown in FIG. 1, the ultrasonic imaging system 100 includes an ultrasonic probe 110, a transmitting circuit 112, a receiving circuit 114, a processor 116 and a display 118. Further, the ultrasonic imaging system may also include a transmitting/receiving switch 120 and a beam former 122. The transmitting circuit 112 and the receiving circuit 114 may be connected to the ultrasonic probe 110 through the transmitting/receiving switch 120.

The ultrasonic probe 110 includes a plurality of transducers. The plurality of transducers may be arranged in a row to form a linear array, or arranged in a two-dimensional matrix to form a matrix array. The plurality of transducers may also form a convex array. The transducers can transmit ultrasonic waves according to the excitation electrical signals, or convert the received ultrasonic waves into electrical signals. Therefore, each transducer can realize the mutual conversion of electrical pulse signals and ultrasonic waves, so as to realize the transmitting of the ultrasonic waves to the target area of the object to be examined and receiving of the ultrasonic echoes reflected by the tissue. When performing ultrasonic examination, which transducers will be used to transmit the ultrasonic waves and which transducers will be used to receive the ultrasonic echoes can be determined by the transmitting sequence and the receiving sequence. Alternatively, the transducers may be used to transmit the ultrasonic waves and receive the ultrasonic echoes in a time-share manner. The transducers participating in the ultrasonic transmitting may be excited by electrical signals at the same time, thereby simultaneously transmitting the ultrasonic waves. Alternatively, the transducers participating in the ultrasonic transmitting may be excited by electrical signals with certain time intervals, thereby continuously transmitting ultrasonic waves with certain time intervals.

In the ultrasonic imaging, the transmitting circuit 112 sends the transmitting pulses that have been delay-focused to the ultrasonic probe 110 through the transmitting/receiving switch 120. The ultrasonic probe 110 is excited by the transmitting pulses to transmit an ultrasonic beam to the tissue in the target area of the object to be examined, receives the ultrasonic echoes with tissue information reflected from the tissue in the target area after a certain delay, and converts the ultrasonic echoes into electrical signals. The object to be examined may be a person. Alternatively, the object to be examined may be an animal, such as a cat, a dog, a rabbit, etc. The receiving circuit 114 receives the electrical signals converted by the ultrasonic probe 110 to obtain ultrasonic echo signals, and sends the ultrasonic echo signals to the beam former 122. The beam former 122 performs processing such as delay-focusing, weighting and channel summation, etc. on the ultrasonic echo signals, and then sends them to the processor 116. The processor 116 performs processing such as signal detection, signal enhancement, data conversion and logarithmic compression, etc. on the ultrasonic echo signals to form an ultrasonic image. The ultrasonic image obtained by the processor 116 may be displayed on the display 118 or stored in a memory 124.

Alternatively, the processor 116 may be implemented as software, hardware, firmware, or any combination thereof, and may use single or multiple Application Specific Integrated Circuits (ASICs), single or multiple general purpose integrated circuits, single or multiple microprocessors, single or multiple programmable logic devices, or any combination of the foregoing circuits and/or devices, or other suitable circuits or devices. The processor 116 may control other components in the ultrasonic imaging system 100 to perform the corresponding steps of the methods in the various embodiments of the present disclosure.

The display 118 is connected to the processor 116. The display 118 may be a touch display screen, a liquid crystal display screen, etc. Alternatively, the display 118 may be an independent display such as a liquid crystal display or a television independent of the ultrasonic imaging system 100. Alternatively, the display 118 may be a display screen for electronic devices such as smart phones and tablet computers, etc. There may be one or more display 118. For example, the display 118 may include a main screen and a touch screen. The main screen may be mainly used to display ultrasonic images, and the touch screen may be mainly used for human-machine interaction.

The display 118 can display the ultrasonic image obtained by the processor 116. In addition, the display 118 can also provide the user with a graphical interface for human-machine interaction while displaying the ultrasonic image. One or more control objects are arranged on the graphical interface, and the user can use the human-machine interaction device to input operation instructions to control these control objects, so as to perform corresponding control operations. For example, a map may be displayed on the graphical interface, and may be operated with the human-machine interaction device to perform specific functions, such as drawing a region of interest box on the ultrasonic image, etc.

Optionally, the ultrasonic imaging system 100 may further include other human-machine interaction device other than the display 118 which is connected to the processor 116. For example, the processor 116 may be connected to the human-machine interaction device through an external input/output port. The external input/output ports may be a wireless communication module, a wired communication module, or a combination thereof. The external input/output port may also be implemented based on USB, bus protocols such as CAN, and/or wired network protocols, etc.

The human-machine interaction device may include an input device for detecting the input information of the user. The input information may be, for example, a control command for the timing of ultrasonic transmitting/receiving, an operation input instruction for drawing a point, a line or a box, etc. on the ultrasonic image, or other type of instruction. The input device may include one of a keyboard, a mouse, a scroll wheel, a trackball, a mobile input device (such as a mobile device with touch screen, a cell phone, etc.), a multi-function knob, etc., or any combination thereof. The human-machine interaction device may further include an output device such as a printer, etc.

The ultrasonic imaging system 100 may include a memory 124 for storing the instructions to be executed by the processor, received ultrasonic echo data, the ultrasonic images, and the like. The memory may be a flash memory card, a solid state memory, a hard disk, etc. The memory may be a volatile memory and/or a non-volatile memory. The memory may be a removable memory and/or a non-removable memory, etc.

It should be understood that the components included in the ultrasonic imaging system 100 shown in FIG. 1 are only illustrative. The ultrasonic imaging system 100 may include more or fewer components, which will not be limited in the present disclosure.

A viscoelasticity measurement method according to an embodiment of the present disclosure will be described with reference to FIG. 2, which is a schematic flowchart of the viscoelasticity measurement method 200 according to the embodiment of the present disclosure.

As shown in FIG. 2, the viscoelasticity measurement method 200 may include the following steps.

In step S210, a shear wave propagating in the target area of the object to be examined is generated.

In step S220, ultrasonic waves tracking the shear wave are transmitted to the target area, and the ultrasonic echoes returned from the target area are received to obtain ultrasonic echo data.

In step S230, the tissue motion information in the propagation of the shear wave is obtained according to the ultrasonic echo data.

In step S240, tissue motion target information corresponding to at least two shear waves of different frequencies is obtained from the tissue motion information.

In step S250, tissue motion target information corresponding to the at least two shear waves of different frequencies is output, where the tissue motion target information represents the viscosity characteristic of the target area.

The viscosity of the tissue will cause the frequency dispersion effect of the shear wave in the tissue, which will lead to different propagation of the shear waves of different frequency components in the tissue. On the basis of the elasticity measurement, in the viscoelasticity measurement method 200 of the embodiment of the present disclosure, extracting tissue motion target information corresponding to at least two shear waves of different frequencies related to the shear wave frequency dispersion effect from the tissue motion information is added. The tissue motion target information of at least two shear waves of different frequencies reflects the viscous characteristics of the tissue.

Illustratively, before performing step S210, the tissue structure image of the object to be examined may be first obtained, and the region of interest for viscoelasticity measurement may be determined according to the tissue structure image of the object to be examined.

Referring to FIG. 1, the processor 116 controls the transmitting circuit 112 to transmit the delay-focused transmitting pulses to the ultrasonic probe 110 through the transmitting/receiving switch 120. The ultrasonic probe 110 is excited by the transmitting pulses to transmit an ultrasonic beam to the tissue in the target area of the object to be examined, receives the ultrasonic echoes carrying tissue information returned from the tissue in the target area after a certain delay, and converts the ultrasonic echoes into electrical signals. The receiving circuit 114 receives the electrical signals converted by the ultrasonic probe 110 to obtain ultrasonic echo signals, and sends the ultrasonic echo signals to the beam former 122. The beam former 122 performs processing such as focus-delay, weighting and channel summation, etc. on the ultrasonic echo signals, and then sends the ultrasonic echo signals to the processor 116. The processor 116 performs processing such as signal detection, signal enhancement, data conversion and logarithmic compression, etc. on the ultrasonic echo signals to form tissue structure image, such as B mode image, C mode image, etc.

Thereafter, the position of the region of interest can be determined according to the tissue structure image. In one example, the tissue structure image can be displayed on a display, the region of interest on the tissue structure image can be manually determined by the user, and the position of the region of interest can be determined according to detected user input.

In another example, the position of the region of interest may be automatically determined on the tissue structure image using relevant machine recognition algorithm. Alternatively, the region of interest may be determined by semi-automatic detection. For example, first, the position of the region of interest on the tissue structure image may be automatically detected using the machine recognition algorithm, and then, it may be further modified or corrected by the user to obtain a more accurate position of the region of interest.

Next, an acoustic radiation force impact can be performed to the target area of the object to be examined according to the position of the region of interest determined by the method above using a preset pulse sequence to generate a shear wave. Specifically, the ultrasonic probe transmits special ultrasonic push pulses to the tissue in the region of interest of the object to be examined to generate the shear wave propagating in the tissue based on the acoustic radiation force. The length of the ultrasonic push pulse is generally greater than 100 us. Since the shear wave generated by the acoustic radiation force pulse itself has a small amplitude, and the shear wave will decay rapidly with propagation, multiple ultrasonic push pulses can be continuously transmitted in order to enhance the intensity and range of the generated shear wave.

Alternatively, the spectral range of the generated shear wave can be adjusted by continuously transmitting the ultrasonic push pulses multiple times and adjusting the interval of the transmitting of the ultrasonic push pulses. For example, the ultrasonic push pulses may be continuously transmitted multiple times at a certain time interval PRT (for example, 5 ms). In this case, the frequency of the generated shear wave will be concentrated at the frequency point of N/PRT (for example, 200 Hz, 400 Hz, 600 Hz . . . etc.), where the frequency component at the frequency point of 1/PRT is the strongest, that is, it is the main frequency of the shear wave. Therefore, shear waves of different frequencies can be generated by changing the length of the PRT.

Thereafter, the ultrasonic probe continuously transmits a series of ultrasonic waves for tracking the shear wave to the tissue in the region of interest for a period of time (for example, tens of milliseconds), and receives the ultrasonic echoes to obtain ultrasonic echo data. The tissue motion information during the propagation of the shear wave may be obtained according to the ultrasonic echo data. The tissue motion information obtained thereby includes the tissue motion information of multiple shear waves of different frequencies within 0~1000 Hz, and the tissue motion information of each shear wave frequency component can be regarded as information characterizing the tissue vibration state caused by the shear wave of one frequency. Referring to FIG. 3 which shows a spectrogram of the tissue motion information in a wide frequency band, the tissue motion information includes multiple shear wave components within 0~1000 Hz, so the spectrogram has a high amplitude in a wide frequency band.

Specifically, the tissue motion information during the propagation of the shear wave in the tissue can be calculated by the processor of the ultrasonic imaging system according to the above-mentioned ultrasonic echo data. According to the wave characteristics, when the shear wave propagates through a certain position in the tissue, the tissue at said position will vibrate. When the shear wave propagates away from the position, the tissue at said position will return to its original state. Therefore, by performing correlation between the ultrasonic echo data obtained at different times, the tissue motion information over a period of time can be obtained. The tissue motion information may be tissue displacement, tissue motion velocity, tissue acceleration, tissue strain variables, etc., or be data obtained by further performing filtering, differentiation or integration, etc. on the variables above.

The correlation may be performed between the ultrasonic echo signals obtained at adjacent times, or between the ultrasonic echo signals at different times and the ultrasonic echo signals at a reference time. The correlation algorithm may be a general algorithm for conventional tissue displacement detection, such as the cross-correlation algorithm based on block matching, the calculation method based on Doppler frequency shift and the method based on phase shift detection, etc. The embodiments of the present disclosure will not limit the specific algorithms used for detecting the tissue motion information.

Figure 4:
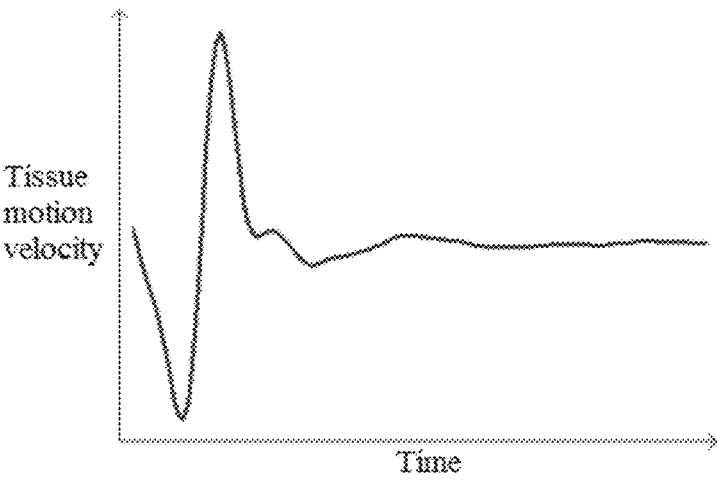
FIG. 4 shows the vibration waveform of the tissue motion information according to an embodiment of the present disclosure.

Optionally, by aggregating the tissue motion information caused by the shear waves at different times, the tissue vibration waveform can be observed. FIG. 4 shows the tissue motion velocity-time curve at a certain position in the tissue over a period of time. Alternatively, the tissue vibration waveform can also be observed by aggregating other tissue motion information described above over a period of time, for example, by plotting tissue displacement-time curves, etc.

In step S240, tissue motion target information corresponding to at least two shear waves of different frequencies is extracted from the tissue motion information. The tissue motion target information corresponding to the shear waves of different frequencies extracted from the tissue motion information can be regarded as tissue motion information caused by the shear waves of different frequencies. By extracting the tissue motion target information corresponding to the shear waves of different frequencies from the tissue motion information, the tissue motion target information corresponding to shear waves of different frequencies can be obtained by only one time of acoustic radiation force pulse transmitting, so as to be analyzed to represent the viscosity characteristics of the tissue without the need for multiple transmitting and receiving.

In one embodiment, the tissue motion target information of at least two shear waves of different frequencies may be extracted by filtering the tissue motion information. The filtering may be performed in the time domain, frequency domain or using various algorithms. The algorithm may be a convolution operation, etc. Of course, the filtering process may also include a series of processing procedures before or after the filtering, which is not specifically limited herein.

As described above, the tissue motion information may be a time domain signal describing the change of tissue motion information in the region of interest over time, and the filtering on the tissue motion information may be performed in the time domain, that is, time domain filtering may be performed on the tissue motion information.

As another implementation, the tissue motion information may also be converted into frequency domain signals, and the frequency domain filtering may be performed thereon. For example, the amplitudes in the frequency bands other than the desired frequency band in the frequency domain signal may be set to zero. Thereafter, the frequency domain signal filtered in frequency domain may be inversely converted into a time domain signal. Exemplarily, the conversion of the tissue motion information from the time domain to the frequency domain may be achieved by Fourier transform, and the conversion of the tissue motion information from the frequency domain to the time domain may be achieved by inverse Fourier transform.

In one embodiment, the tissue motion target information may be extracted using various suitable filters, which may be software filters or hardware filters additionally provided in the ultrasonic imaging system.

Illustratively, as a more accurate filtering method, the filtering may be performed with different frequencies as the center frequencies using at least two band-pass filters of different frequencies to extract the tissue motion target information corresponding to the shear waves of the corresponding frequencies. For example, 300 Hz and 600 Hz band-pass filters may be respectively used to extract the tissue motion target information with 300 Hz and 600 Hz as the center frequencies from the wide-band tissue motion information of 0~1000 Hz. It can be understood that when performing a filtering with a band-pass filter, two or more band-pass filters may be used to extract tissue motion target information corresponding to shear waves of multiple frequencies from the tissue motion information.

In addition, as a relatively simplified filtering method, a low-pass filter and a high-pass filter may be used to filter the tissue motion information respectively so as to extract the low-frequency components and the high-frequency components in the tissue motion information as two different types of tissue motion information. For example, 500 Hz high-pass filter and low-pass filter may be used to extract the low-frequency components of 0~500 Hz and high-frequency component of 500~1000 Hz from a wide-band tissue motion information of 0~1000 Hz.

The extracted tissue motion target information does not include only the single frequency of the center frequency, but includes a frequency band with a preset frequency point as the center frequency. By adjusting the parameter of the filter used for filtering, the bandwidth of the shear wave frequency of the extracted tissue motion target information can be changed. The more concentrated the shear wave frequency of the extracted tissue motion target information, the more accurate the obtained tissue motion target information at the current shear wave frequency. However, correspondingly, due to the large amount of tissue motion information filtered out, the signal to noise ratio of the obtained signal will decrease. Therefore, by adjusting the parameter of the filter, the desired balance can be obtained between the accuracy of the tissue motion target information and the signal to noise ratio of the signal.

In some embodiments, since the tissue motion information is related to the frequency of the shear wave, the frequency information of at least two shear waves of different frequencies may also be output. For example, the frequency information of at least two shear waves of different frequencies may be output while the tissue motion target information of at least two shear waves of different frequencies is output.

In step S250, the tissue motion target information corresponding to at least two shear waves of different frequencies is output. The tissue motion target information corresponding to shear waves of different frequencies is used to reflect the viscosity characteristics of the tissue.

In order to present the viscous state of the tissue more vividly, the tissue motion target information corresponding to shear waves of different frequencies may be output in a graphical manner. Alternatively, in order to quantitatively present the viscous state of the tissue, the tissue motion target information corresponding to at least two shear waves of different frequencies may be output numerically.

When the tissue motion target information is output in a graphical manner, a tissue motion image can be generated according to the tissue motion target information corresponding to at least two shear waves of different frequencies, and be displayed. Several exemplary tissue motion images are shown below in FIGS. 5A, 5B, 6A and 6B.

Figure 5A:
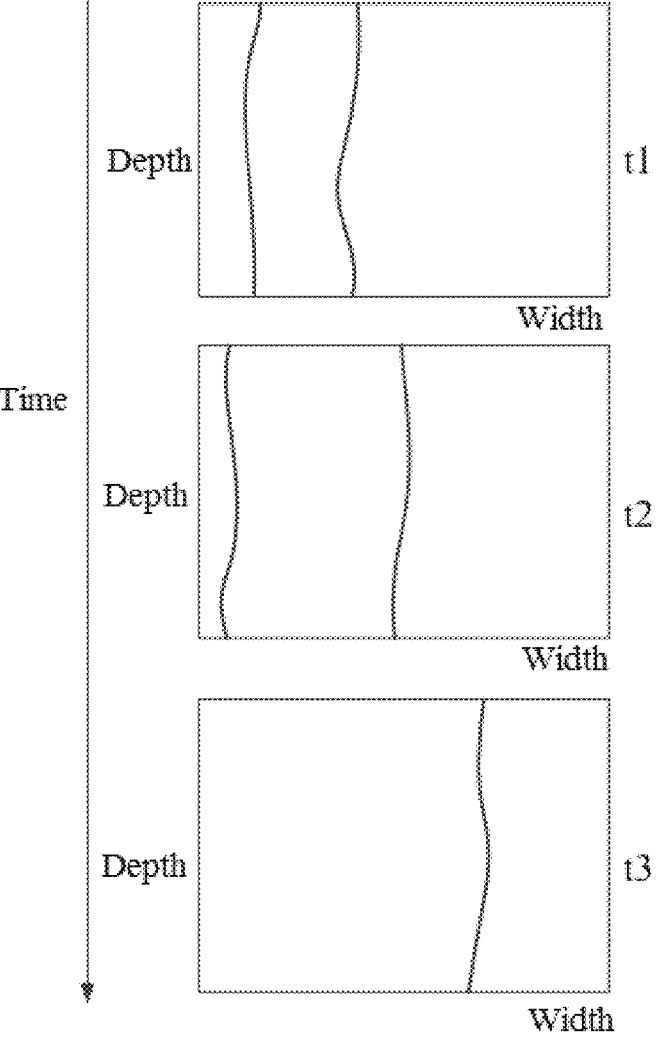
FIG. 5A and FIG. 5B show tissue motion images according to an embodiment of the present disclosure.
Figure 5B:
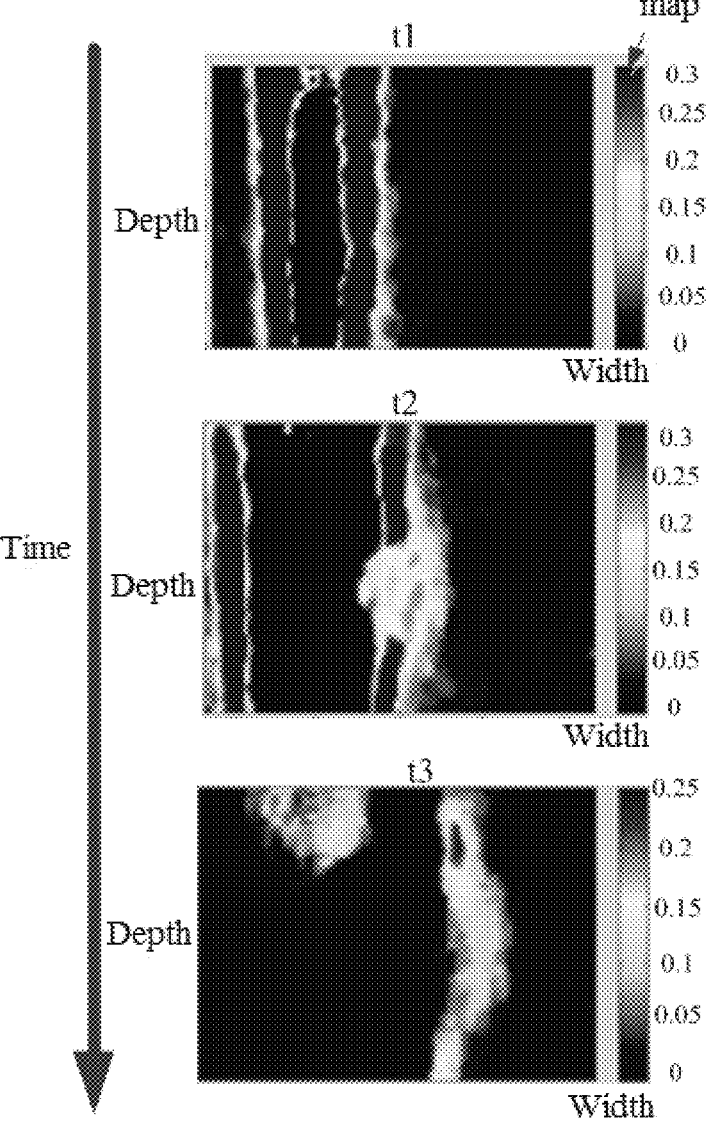

As shown in FIG. 5A and FIG. 5B, in one embodiment, the tissue motion image includes at least one frame, and each frame of tissue motion image represents the tissue motion target information corresponding to the shear wave of at least one frequency at a preset time. The three frames of tissue motion images shown in FIG. 5A represent the tissue motion target information at times t1, t2 and t3, respectively. The abscissa is in the width direction and the ordinate is in the depth direction. The curve in each frame of tissue motion image represents the shear wave propagation state at the current time. Affected by tissue viscosity, the propagation states of the shear waves of different frequencies are different. In FIG. 5A, the tissue motion information is abstracted into curve. In other examples, the tissue motion information at the positions of the image, such as the magnitudes of the tissue displacement or the magnitudes of the tissue motion velocity at the positions of the image, may be represented in different colors or grays, etc. For example, the tissue motion target information at times t1, t2 and t3 is shown in FIG. 5B in different grays.

In FIG. 5A and FIG. 5B, each frame of tissue motion image represents the tissue motion target information corresponding to the shear wave of one frequency at a preset time, where the frames of tissue motion image corresponding to the shear wave of different frequencies at the same preset time are displayed in different windows simultaneously. In other examples, each frame of tissue motion image may also represent the tissue motion target information corresponding to at least two shear waves of different frequencies at a preset time, and the frames of tissue motion images corresponding to at least two shear waves of different frequencies at different times are displayed in the same window. The tissue motion target information corresponding to shear waves of different frequencies may be displayed differently by one of map, color and line.

In the case that the tissue motion image includes at least two frames, displaying the tissue motion image may include dynamically displaying the at least two frames of tissue motion images in chronological order, that is, displaying the tissue motion image in the form of a video according to a preset frame rate. Alternatively, the at least two frames of tissue motion images may be displayed cumulatively in chronological order. For example, as shown in FIG. 5A and FIG. 5B, multiple frames of tissue motion images are displayed cumulatively on the display interface in chronological order.

Figure 6A:
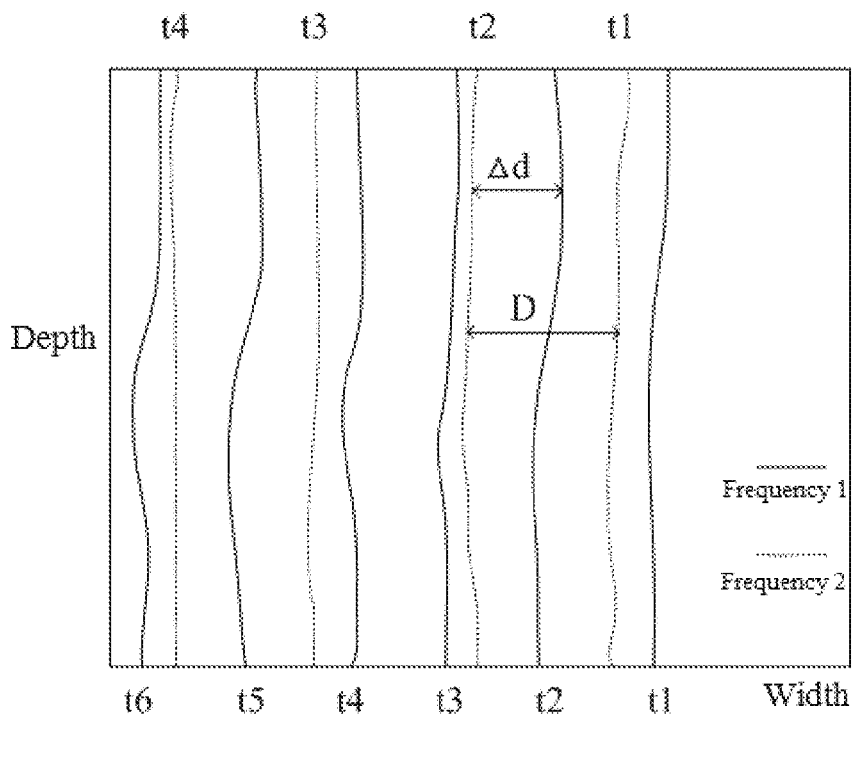
FIG. 6A shows a tissue motion image according to another embodiment of the present disclosure.

In another embodiment, as shown in FIG. 6A, one frame of tissue motion image may simultaneously represent the tissue motion target information of at least two shear waves of different frequencies at a plurality of preset times.

The abscissa and ordinate of the tissue motion image shown in FIG. 6A correspond to the width direction and depth direction of the tissue, respectively. Based on the tissue motion target information corresponding to the shear wave of each frequency, the propagation position of the shear wave at each preset time can be calculated. The curve representing the propagation positions of the shear wave can be drawn on a same tissue motion image, so as to obtain a static tissue motion image shown in FIG. 6A. In FIG. 6A, the propagation positions of the shear wave is abstracted as a curve, where the solid line and the dashed line correspond to two shear waves of different frequencies, namely the first frequency and the second frequency. Optionally, it is also possible to display the tissue motion target information of shear waves of different frequencies differently by at least one of map, color or line. If the shear wave of a certain frequency propagates faster, it can be observed that at the same moment, its propagation position is further ahead and the distance difference between shear waves of different frequencies will appear. Generally, the stronger the viscosity of the tissue, the greater the distance difference between two shear waves of different frequencies. Thereby, the viscosity of the tissue may be determined according to the tissue motion image.

Illustratively, the intervals between the preset times in tissue motion images may be equal, such as 1 ms, 2 ms or 3 ms, etc. For example, for the tissue with uniform viscoelasticity, the propagation velocity of the shear wave will be uniform. Therefore, the propagation distance of the shear wave within equal time intervals will also be uniform. Accordingly, it is possible to intuitively determine whether the viscoelasticity of the tissue is uniform according to the tissue motion image. Alternatively, the intervals between the preset times may also be unequal.

Figure 6B:
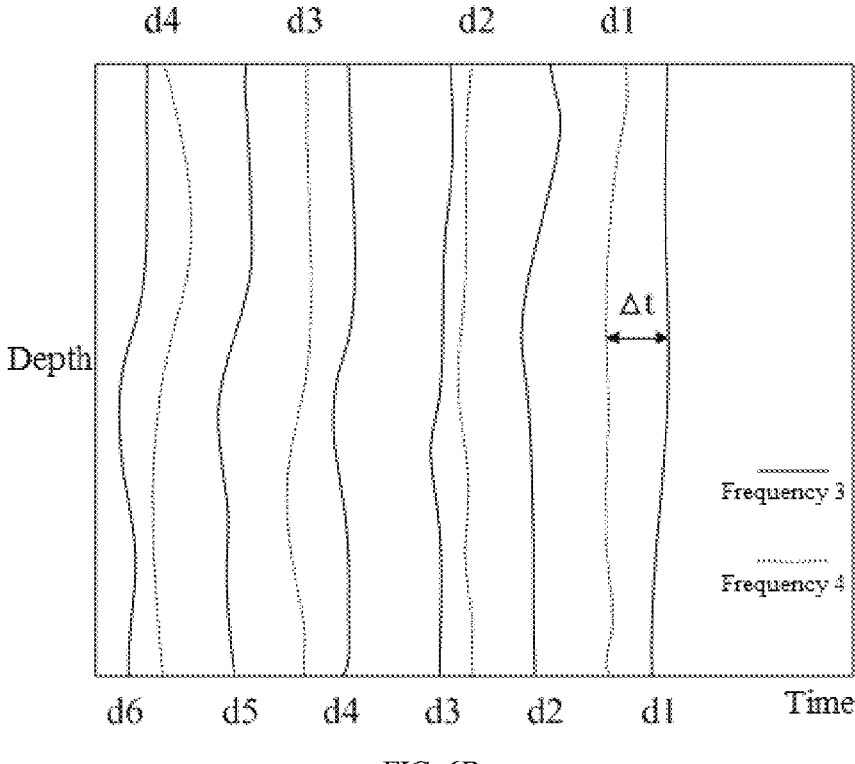
FIG. 6B shows a tissue motion image according to another embodiment of the present disclosure.

Alternatively, the tissue motion image may represent the time information required for at least two shear waves of different frequencies to propagate to at least two preset propagation positions, as shown in FIG. 6B. The tissue motion image shown in FIG. 6B is similar to the tissue motion image shown in FIG. 6A, except that the abscissa and ordinate of the tissue motion image shown in FIG. 6B correspond to the propagation time and depth, respectively. In FIG. 6B, the different lines correspond to the time required for shear waves of different frequencies to propagate to different propagation distances, where the solid line corresponds to a third frequency, and the dashed line corresponds to a fourth frequency. However, in addition to differently displaying the tissue motion target information of shear waves of different frequencies with different lines, the tissue motion target information of shear waves of different frequencies may also be differently displayed through at least one of map and color. If the shear wave of a certain frequency propagates faster, it can be observed that for the same propagation distance, the time required is shorter. Generally, the stronger the viscosity of the tissue, the greater the difference in propagation time between two shear waves of different frequencies.

When the tissue motion target information of at least two shear waves of different frequencies is output numerically, a parameter representing the viscous characteristics of the target area may be generated according to the tissue motion target information of at least two shear waves of different frequencies, and be displayed. The parameter may be obtained according to the above-mentioned tissue motion image, and the tissue motion image may be output together with the parameter. Alternatively, it may also be possible to only obtain the parameter according to the tissue motion information, but not display the tissue motion image.

Illustratively, the parameter may include at least one of: the distance between the propagation positions of shear waves of different frequencies at the same moment; the ratio between said distance and the propagation distance of the shear wave of one of the different frequencies within a preset time; and the time difference between the times required for the shear waves of different frequencies to propagate to the same preset propagation position. Illustratively, referring to FIG. 6A, since the stronger the viscosity of the tissue, the greater the difference between the propagation distances of two shear waves of different frequencies, the parameter may be the distance $\Delta d$ between two shear waves of different frequencies at the same moment in FIG. 6A. Alternatively, the parameter may also be related to the propagation distances of the shear waves of different frequencies within the same time period (that is, the propagation distance D of the shear wave frequency component represented by the dotted line in FIG. 6A within the time period t1 to t2). Alternatively, the parameter may be the ratio $\Delta d/D$ between $\Delta d$ and D. since the stronger the viscosity of the tissue, the greater the difference between the propagation velocities of two shear waves of different frequencies, the parameter may also be time difference between the times required for shear waves of different frequencies to propagate to the same preset propagation position. For example, referring to FIG. 6B, the time difference may be the time difference $\Delta t$ between the times required for the shear waves of the third frequency and the fourth frequency to propagate to d1.

Since the propagation state of the shear wave is affected by the viscosity of the tissue, the parameter may also be other parameter related to the propagation distance, propagation velocity, propagation time, etc. of the shear wave.

A viscoelasticity measurement method 200 according to one embodiment of the present disclosure has been described above. Based on the above description, in the viscoelasticity measurement method 200 according to the embodiment of the present disclosure, the viscous characteristics of the tissue may be represented through the tissue motion target information of at least two shear waves of different frequencies.

The embodiment of the present disclosure also provides an ultrasonic imaging system that can be used for realizing the above-mentioned viscoelasticity measurement method 200. The ultrasonic imaging system includes an ultrasonic probe, a transmitting circuit, a receiving circuit, a processor and a display. Referring again to FIG. 1, the ultrasonic imaging system may be implemented as the ultrasonic imaging system 100 shown in FIG. 1. As described above, the ultrasonic imaging system 100 may include an ultrasonic probe 110, a transmitting circuit 112, a receiving circuit 114, a processor 116 and a display 118. The ultrasonic imaging system may also include a transmitting/receiving switch 120 and a beam former 122. Regarding the descriptions of the various components, reference may be made to the description above.

Specifically, the ultrasonic probe 110 is configured to generate the shear waves propagating in the target area of the object to be examined. The transmitting circuit 112 is configured to excite the ultrasonic probe 110 to transmit the ultrasonic waves tracking the shear waves to the target area. The receiving circuit 114 is configured to control the ultrasonic probe 110 to receive the ultrasonic echoes returned from the target area to obtain ultrasonic echo data. The processor 116 is configured to execute the steps of the viscoelasticity measurement method 200, namely: obtaining the tissue motion information during the propagation of the shear waves according to the ultrasonic echo data; extracting tissue motion target information corresponding to shear waves of at least two different frequencies from the tissue motion information; and controlling the display 118 to output the tissue motion target information corresponding to the shear waves of at least two different frequencies, where the tissue motion target information represents the viscosity characteristic of the target area.

In one embodiment, the processor 116 may be configured to control the display 118 to output the tissue motion target information corresponding to the shear waves of at least two different frequencies in a graphical or numerical manner.

In one embodiment, the processor 116 may be further configured to generate the tissue motion image according to the tissue motion target information of the shear waves of at least two different frequencies, and control the display 118 to display the tissue motion image.

In one embodiment, the tissue motion image includes at least one frame, and each frame of the tissue motion image represents the tissue motion target information corresponding to the shear waves of at least one frequency at a preset time.

In another embodiment, one frame of tissue motion image may simultaneously represent the tissue motion target information corresponding to the shear waves of at least two different frequencies at a plurality of preset times.

In another embodiment, the tissue motion image may represent the time information required for the shear waves of at least two different frequencies to propagate to at least two predetermined propagation positions.

In one embodiment, the processor 116 may be further configured to generate the parameter representing the viscosity characteristic of the target area according to the tissue motion target information of the at least two shear waves of different frequencies, and control the display 118 to display the parameter.

Illustratively, the parameter may include at least one of: the distance between the propagation positions of shear waves of different frequencies at the same moment; the ratio between the distance and the propagation distance of the shear wave of one frequency within a preset time period; and the time difference between the times required for the shear waves of different frequencies to propagate to the same preset propagation position.

In the description above, only the main functions of the components of the ultrasonic imaging system 100 have been described. Regarding more details, reference may be made to the related description of the viscoelasticity measurement method 200. The ultrasonic imaging system in the embodiments of the present disclosure can represent the viscosity characteristics of the tissue through the tissue motion target information of the shear waves of at least two different frequencies.

A viscoelasticity measurement method according to another embodiment of the present disclosure will be described below with reference to FIG. 7 that shows a schematic flowchart of a viscoelasticity measurement method 700. As shown in FIG. 7, the viscoelasticity measurement method 700 includes the following steps.

In step S710, the shear waves of at least two different frequencies propagating in the target area of the object to be examined can be generated.

In step S720, the ultrasonic waves for tracking the shear waves of at least two different frequencies are transmitted to the target area, and the ultrasonic echoes returned from the target area are received to obtain ultrasonic echo data.

In step S730, the tissue motion target information corresponding to the shear waves of at least two different frequencies is obtained according to the ultrasonic echo data.

In step S740, the tissue motion target information corresponding to the shear waves of at least two different frequencies is outputted, where the tissue motion target information represents the viscosity characteristic of the target area.

The viscoelasticity measurement method 700 shown in FIG. 7 differs from the above-mentioned viscoelasticity measurement method 200 in that the viscoelasticity measurement method 700 does not extract the tissue motion target information of shear waves of different frequencies from the tissue motion information, but directly generates shear waves of at least two different frequencies in step S710. Specifically, shear waves of different frequencies may be generated by adjusting the transmission interval of the ultrasonic push pulses. For example, the ultrasonic push pulses may be continuously transmitted several times in a certain time interval PRT. The frequency of the generated shear waves generated thereby will be concentratedly distributed on the frequency point of N/PRT. Therefore, shear waves of different frequencies may be generated by changing the length of the PRT. Alternatively, the instantaneous elastography method may be used, in which the vibrator in the ultrasonic probe generates vibration of different frequencies to generate shear waves of different frequencies.

For the shear wave of each frequency, the ultrasonic waves tracking said shear wave are transmitted to the target area, and the ultrasonic echoes returned from the target area are received to obtain ultrasonic echo data. The tissue motion target information corresponding to the shear waves of at least two frequencies is obtained according to the ultrasonic echo data corresponding to the shear waves of at least two different frequencies. Finally, the tissue motion target information corresponding to the shear wave of at least two different frequencies is output. In some embodiments, since the tissue motion information is related to the frequency of the shear wave, the frequency information of the shear waves of at least two different frequencies may also be output. For example, the frequency information of the shear waves of at least two different frequencies may be output while the tissue motion target information of the shear waves of at least two different frequencies is output.

Illustratively, outputting the tissue motion target information corresponding to the shear waves of at least two different frequencies may include outputting the tissue motion target information corresponding to the shear waves of at least two different frequencies in a graphical or numerical manner. Outputting the tissue motion target information corresponding to the shear waves of at least two different frequencies in a graphical manner may include generating the tissue motion image according to the tissue motion target information corresponding to the shear waves of at least two different frequencies and displaying the tissue motion image. Outputting the tissue motion target information corresponding to the shear waves of at least two different frequencies in a numerical manner may include generating the parameter representing the viscosity characteristic of the target area according to the tissue motion target information corresponding to the shear waves of at least two different frequencies and displaying the parameter. The form of the tissue motion image and the type of the parameter may be similar to those in the viscoelasticity measurement method 200. For details, reference may be made to the description above, which will not be described again here.

The viscoelasticity measurement method 700 according to the embodiment of the present disclosure can represent the viscosity characteristics of the tissue according to the tissue motion target information corresponding to the shear waves of at least two different frequencies.

The embodiment of the present disclosure also provides an ultrasonic imaging system for realizing the above-mentioned viscoelasticity measurement method 700. The ultrasonic imaging system includes an ultrasonic probe, a transmitting circuit, a receiving circuit, a processor and a display. Referring again to FIG. 1, the ultrasonic imaging system may be implemented as the ultrasonic imaging system 100 as shown in FIG. 1. As described above, the ultrasonic imaging system 100 may include an ultrasonic probe 110, a transmitting circuit 112, a receiving circuit 114, a processor 116 and a display 118. The ultrasonic imaging system may also include a transmitting/receiving switch 120 and a beam former 122. Regarding the description of the various components, reference may be made to the description above.

Specifically, the ultrasonic probe 110 is configured to generate the shear waves of at least two different frequencies propagating in the target area of the object to be examined. The transmitting circuit 112 is configured to excite the ultrasonic probe 110 to transmit the ultrasonic waves for tracking the shear waves of at least two different frequencies to the target area. The receiving circuit 114 is configured to control the ultrasonic probe 110 to receive the ultrasonic echoes returned from the target area to obtain the ultrasonic echo data. The processor 116 is configured to obtain the tissue motion target information corresponding to the shear waves of at least two different frequencies according to the ultrasonic echo data and control the display 118 to output the tissue motion target information corresponding to the shear waves of at least two different frequencies, where the tissue motion information represents the viscosity characteristic of the target area.

In one embodiment, outputting the tissue motion information of the shear waves of at least two different frequencies during the propagation thereof may include outputting the tissue motion target information corresponding to the shear waves of at least two different frequencies in a graphical or numerical manner.

In one embodiment, the processor 116 may be further configured to generate the tissue motion image according to the tissue motion target information corresponding to the shear waves of at least two different frequencies, and outputting the tissue motion target information corresponding to the shear waves of at least two different frequencies in a graphical manner may include controlling the display 118 to display the tissue motion image.

In one embodiment, the processor 116 may be further configured to generate the parameter representing the viscosity characteristic of the target area according to the tissue motion target information corresponding to the shear waves of at least two different frequencies, and outputting the tissue motion target information corresponding to the shear waves of at least two different frequencies in a numerical manner may include controlling the display 118 to display the parameter.

In the description above, only the main functions of the components of the ultrasonic imaging system 100 have been described. Regarding more details, reference may be made to the related description of the viscoelasticity measurement method 700. The ultrasonic imaging system in the embodiments of the present disclosure can represent the viscosity characteristics of the tissue through the tissue motion target information of the shear waves of at least two different frequencies.

A viscoelasticity measurement method according to another embodiment of the present disclosure will be described below with reference to FIG. 8 that shows a schematic flowchart of a viscoelasticity measurement method 800. As shown in FIG. 8, the viscoelasticity measurement method 800 of the embodiment of the present disclosure includes the following steps.

In step S810, the shear wave propagating in the target area of the object to be examined may be generated.

In step S820, the ultrasonic waves tracking the shear wave may be transmitted to the target area, and the ultrasonic echoes returned from the target area may be received to obtain the ultrasonic echo data.

In step S830, the tissue motion information corresponding to the shear wave may be obtained according to the ultrasonic echo data.

In step S840, the tissue motion target information corresponding to the shear waves of at least two different frequencies may be extracted from the tissue motion information.

In step S850, the parameter representing the viscosity characteristic of the target area may be generated according to the tissue motion target information corresponding to the shear waves of at least two different frequencies, and be displayed.

The viscoelasticity measurement method 800 shown in FIG. 8 differs from the viscoelasticity measurement method 200 above in that in the viscoelasticity measurement method 800 the parameter can be directly generated according to the tissue motion target information corresponding to the shear waves of at least two different frequencies. Illustratively, in the viscoelasticity measurement method 800, there is no need to generate a new parameter (for example, shear wave velocity, etc.) according to the tissue motion target information corresponding to the shear waves of at least two different frequencies and then further generate the parameter representing the viscosity based on the new parameter. Instead, after obtaining the tissue motion target information corresponding to the shear waves of at least two different frequencies, the parameter representing the viscosity may be calculated directly according to the tissue motion target information corresponding to the shear waves of at least two different frequencies. In addition, the steps S810 to S840 are substantially similar to the steps S210 to S240 of the viscoelasticity measurement method 200.

In one embodiment, the parameter representing the viscosity may include at least one of: the distance between the propagation positions of shear waves of different frequencies at the same moment; the ratio between said distance and the propagation distance of the shear wave of one of the different frequencies within a preset time; and the time difference between the times required for the shear waves of different frequencies to propagate to the same preset propagation position.

In one embodiment, in addition to outputting the parameter representing the viscosity, the viscoelasticity measurement method 800 may further include outputting the tissue motion target information corresponding to the shear waves of at least two different frequencies. The tissue motion target information may be output in the form of images, including but not limited to the tissue motion image described in the viscoelasticity measurement method 200. The tissue motion target information may also be output in a numerical manner. Illustratively, the parameter in step S850 may be displayed while displaying the tissue motion target information of the shear waves of at least two different frequencies.

In some embodiments, since the tissue motion information is related to the frequency of the shear wave, the frequency information of the shear waves of at least two different frequencies may also be output. For example, the frequency information of the shear waves of at least two different frequencies may be output while outputting the tissue motion target information of the shear waves of at least two different frequencies.

In addition, the viscoelasticity measurement method 800 has many same or similar features as the viscoelasticity measurement method 200 above. Regarding the details, reference may be made to the description above, which will not be described again here. In the viscoelasticity measurement method 800, the parameter representing the viscosity may be generated according to the tissue motion target information corresponding to the shear waves of at least two different frequencies to represent the viscosity characteristics of the tissue.

In the embodiments of the present disclosure, an ultrasonic imaging system is provided, which is configured to realize the viscoelasticity measurement method 800. The ultrasonic imaging system includes an ultrasonic probe, a transmitting circuit, a receiving circuit, a processor and a display. Referring again to FIG. 1, the ultrasonic imaging system may be implemented as the ultrasonic imaging system 100 shown in FIG. 1. As described above, the ultrasonic imaging system 100 may include an ultrasonic probe 110, a transmitting circuit 112, a receiving circuit 114, a processor 116 and a display 118. The ultrasonic imaging system may also include a transmitting/receiving switch 120 and a beam former 122. Regarding the detailed description of the components, reference may be made to the description above.

Specifically, the ultrasonic probe 110 is configured to generate shear waves propagating in the target area of the object to be examined. The transmitting circuit 112 is configured to excite the ultrasonic probe 110 to transmit ultrasonic waves tracking the shear waves to the target area. The receiving circuit 114 is configured to control the ultrasonic probe 110 to receive the ultrasonic echoes returned from the target area to obtain ultrasonic echo data. The processor 116 is configured to obtain the tissue motion information corresponding to the shear waves according to the ultrasonic echo data, extract tissue motion target information corresponding the shear waves of at least two different frequencies from the tissue motion information, generate a parameter representing the viscosity characteristic of the target area according to the tissue motion target information corresponding to the shear waves of at least two different frequencies, and control the display to display the parameter.

In the description above, only the main functions of the components of the ultrasonic imaging system 100 have been described. Regarding more details, reference may be made to the description of the viscoelasticity measurement method 800. The ultrasonic imaging system in the embodiments of the present disclosure can generate the parameter representing the viscosity according to the tissue motion target information corresponding to the shear waves of at least two different frequencies to represent the viscosity of the tissue.

A viscoelasticity measurement method according to another embodiment of the present disclosure will be described below with reference to FIG. 9, which shows a schematic flowchart of a viscoelasticity measurement method 900. As shown in FIG. 9, the viscoelasticity measurement method 900 includes the following steps.

In step S910, shear waves of at least two different frequencies propagating in the target area of the object to be examined are generated.

In step S920, ultrasonic waves for tracking the shear waves of at least two different frequencies are transmitted to the target area, and the ultrasonic echoes returned by from the target area are received to obtain ultrasonic echo data.

In step S930, the tissue motion target information corresponding to the shear waves of at least two different frequencies is obtained according to the ultrasonic echo data.

In step S940, the parameter representing the viscosity characteristic of the target area is generated according to the tissue motion target information corresponding to the shear waves of at least two different frequencies, and is displayed.

The viscoelasticity measurement method 900 shown in FIG. 9 differs from the viscoelasticity measurement method 800 in that in the viscoelasticity measurement method 900 the tissue motion target information of the shear waves of different frequencies is not extracted from the tissue motion information, rather, the shear waves of at least two different frequencies are directly generated in step S910. Specifically, the shear waves of different frequencies can be generated by adjusting the transmitting interval of the ultrasonic push pulses. Alternatively, the transient elastography can be used, in which the vibrator in the ultrasonic probe vibrates in different frequencies to generate the shear waves of different frequencies. Except those, the viscoelasticity measurement method 900 is similar to the viscoelasticity measurement method 800 above, which will not be described again here.

The viscoelasticity measurement method 900 according to the embodiment of the present disclosure can generate the parameter representing the viscosity according to the tissue motion target information corresponding to the shear waves of at least two different frequencies to representing the viscosity characteristics of the tissue.

In an embodiment of the present disclosure, an ultrasonic imaging system is provided, which is configured to realize the viscoelasticity measurement method 900 above. The ultrasonic imaging system includes an ultrasonic probe, a transmitting circuit, a receiving circuit, a processor and a display. Referring again to FIG. 1, the ultrasonic imaging system may be implemented as the ultrasonic imaging system 100 shown in FIG. 1. As described above, the ultrasonic imaging system 100 may include an ultrasonic probe 110, a transmitting circuit 112, a receiving circuit 114, a processor 116 and a display 118. The ultrasonic imaging system 100 may further include a transmitting/receiving switch 120 and a beam former 122. Regarding the detailed descriptions of the various components, reference may be made to the description above.

Specifically, the ultrasonic probe 110 is configured to sequentially generate shear waves of at least two different frequencies propagating in the target area of the subject to be examined. The transmitting circuit 112 is configured to excite the ultrasonic probe 110 to transmit the ultrasonic waves tracking the shear waves of at least two different frequencies to the target area. The receiving circuit 114 is configured to control the ultrasonic probe 110 to receive the ultrasonic echoes returned from the target area to obtain ultrasonic echo data. The processor 116 is configured to obtain the tissue motion target information corresponding to the shear waves of at least two different frequencies according to the ultrasonic echo data, generate parameter representing the viscosity characteristic of the target area according to the tissue motion target information corresponding to the shear waves of at least two different frequencies, and control the display to display the parameter.

The ultrasonic imaging system of the embodiment of the present disclosure can generate parameter representing the viscosity according to the tissue motion target information corresponding to the shear waves of at least different frequencies to represent the viscosity characteristics of the tissue.

Figure 10:
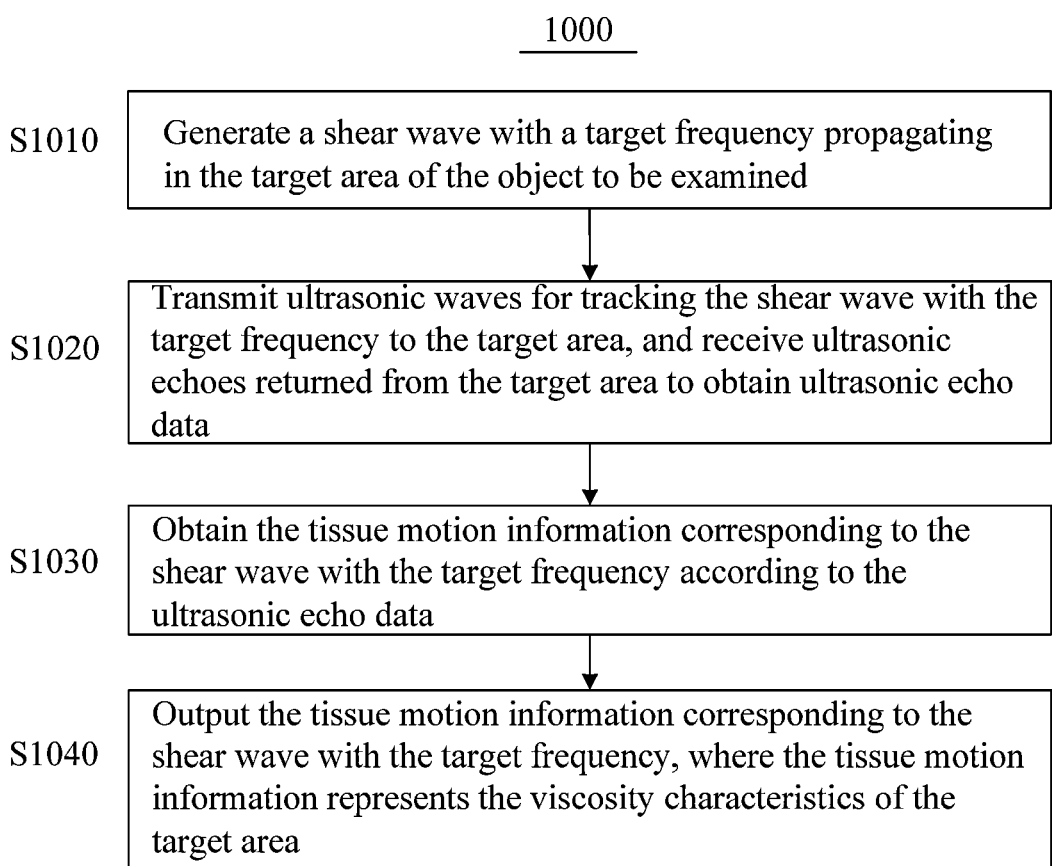
FIG. 10 is a schematic flowchart of a viscoelasticity measurement method according to another embodiment of the present disclosure.

A viscoelasticity measurement method according to another embodiment of the present disclosure will be described below with reference to FIG. 10 which shows a schematic flowchart of a viscoelasticity measurement method 1000. As shown in FIG. 10, the viscoelasticity measurement method 1000 includes the following steps.

In step S1010, the shear wave of a target frequency propagating in the target area of the object to be examined is generated.

In step S1020, the ultrasonic waves for tracking the shear wave of the target frequency are transmitted to the target area, and the ultrasonic echoes returned from the target area are received to obtain the ultrasonic echo data.

In step S1030, the tissue motion information corresponding to the shear wave of the target frequency is obtained according to the ultrasonic echo data.

In step S1040, the tissue motion information corresponding to the shear wave of the target frequency is output, where the tissue motion information is used to represent the viscosity characteristic of the target area.

Similar to the viscoelasticity measurement methods above, the viscoelasticity measurement method 1000 of this embodiment also utilizes the influence of the tissue viscosity to the tissue motion caused by the propagation of shear waves, so as to represent the viscosity characteristics of the tissue according to the tissue motion information. The difference is that the viscoelasticity measurement method 1000 does not represent the viscosity characteristic of the target area through the tissue motion information corresponding to the shear waves of two different frequencies, but represents the viscosity characteristic of the target area through the tissue motion information corresponding to the shear waves of the target frequency. Since for the target areas with different viscosities, the tissue motion information caused by the propagation of shear waves with the same frequency is also different, it is possible to obtain the tissue motion information caused by the shear waves of the target frequency propagating in the reference tissue with known viscosity characteristics in advance, and compare the tissue motion information of the target area with the tissue motion information of the reference tissue so as to determine the viscosity of the target area.

Since the frequency of the shear wave also affects the tissue motion information, in one embodiment, while outputting the tissue motion information corresponding to the shear wave of the target frequency, the frequency information of the shear wave of the target frequency may also be displayed, which will facilitate the user to extract the tissue motion information of the reference tissue at the target frequency obtained in advance.

In some embodiments, the tissue motion information corresponding to the target frequency may be comparatively displayed with the tissue motion information of the reference tissue with known viscosity characteristics so as to represent the viscosity characteristic of the target area. There may be one or more reference tissues, where, each reference tissue has a viscosity characteristic, and the tissue motion information of the target area may be compared with the tissue motion information of various reference tissues so as to find the reference tissue closest to the target area in viscosity characteristic.

In some embodiments, when the target frequency is one frequency, the tissue motion information of the target area at least two different times may be comparatively displayed, and the tissue viscosity may be determined according to the difference between the tissue motion information at different times. For example, the tissue motion information of the target area of the object to be examined at least two different times under one frequency may be obtained, and the tissue viscosity may be determined according to the tissue motion information at least two different times.

The viscoelasticity measurement method 1000 of the embodiment of the present disclosure can represent the viscosity characteristic of the target area through tissue motion information corresponding to the shear wave of the target frequency.

The embodiment of the present disclosure also provides an ultrasonic imaging system for realizing the viscoelasticity measurement method 1000 above. The ultrasonic imaging system may include an ultrasonic probe, a transmitting circuit, a receiving circuit, a processor and a display. Referring again to FIG. 1, the ultrasonic imaging system may be implemented as the ultrasonic imaging system 100 as shown in FIG. 1. As described above, the ultrasonic imaging system 100 may include an ultrasonic probe 110, a transmitting circuit 112, a receiving circuit 114, a processor 116 and a display 118. The ultrasonic imaging system may further include a transmitting/receiving switch 120 and a beam former 122. Regarding the descriptions of the various components, reference may be made to the description above.

Specifically, the ultrasonic probe 110 is configured to generate the shear wave of the target frequency propagating in the target area of the object to be examined. The transmitting circuit 112 is configured to excite the ultrasonic probe 110 to transmit the ultrasonic waves for tracking the shear wave of the target frequency to the target area. The receiving circuit 114 is configured to control the ultrasonic probe 110 to receive the ultrasonic echoes returned from the target area to obtain ultrasonic echo data. The processor 116 is configured to obtain the tissue motion information corresponding to the shear wave of the target frequency according to the ultrasonic echo data, and output the tissue motion information corresponding to the shear wave of the target frequency, where the tissue motion information represents the viscosity characteristic of the target area.

In the description above, only the main functions of the components of the ultrasonic imaging system 100 have been described. Regarding more details, reference may be made to the description of the viscoelasticity measurement method 1000. The ultrasonic imaging system in the embodiments of the present disclosure can represent the viscosity characteristic of the target area through the tissue motion information corresponding to the shear wave of the target frequency.

The embodiments of the present disclosure may also provide a storage medium on which program instructions are stored. The program instructions may be executed by a computer or a processor to perform the steps of the viscoelasticity measurement methods of the embodiments of the present disclosure. The storage medium may be, for example, a memory card of a smart phone, a storage component of a tablet computer, a hard disk of a personal computer, a read-only memory (ROM), an erasable programmable read-only memory (EPROM), a portable compact disk read-only memory (CD-ROM), an USB memory, or any combination thereof. The computer-readable storage medium may be any combination of one or more computer-readable storage media.

In an embodiment of the present disclosure, a computer program is provided, which can be stored on a cloud storage medium or on a local storage medium. When executed by a computer or processor, the computer program can perform the corresponding steps of the viscoelasticity measurement methods of the embodiments of the present disclosure.

Although exemplary embodiments have been described herein with reference to the drawings, it should be understood that the embodiments described above are merely illustrative and not intended to limit the scope of the present disclosure thereto. Various changes and modifications may be made by those of ordinary skill in the art without departing from the scope and spirit of the present disclosure. All such changes and modifications are intended to be included within the scope of the present disclosure as claimed by the appended claims.

Those of ordinary skill in the art will understand that the units and algorithm steps of the examples described in the embodiments of the present disclosure can be implemented by electronic hardware, or by a combination of computer software and electronic hardware. Whether these functions are performed in hardware or software depends on the specific application and design constraints of the technical solutions. Professionals may use different methods to implement the described functions for each particular application, but such implementation should not be considered as beyond the scope of the present disclosure.

It should be understood that the devices and methods disclosed in the embodiments of the present disclosure can be implemented in other ways. For example, the device embodiments described above are merely illustrative, the division of the units is merely a logical function division, and there may be other division methods in actual implementation. For example, multiple units or components can be combined or integrated into another device, or some features can be ignored or not performed.

Specific details have been set forth in the specification herein. However, it should be understood that the embodiments of the present disclosure may be practiced without these specific details. In some embodiments, well-known methods, structures and techniques have not been shown in detail so as not to obscure the understanding to the present disclosure.

Similarly, it should be understood that, in order to streamline the present disclosure and assist in understanding one or more aspects of the present disclosure, in the description of the embodiments of the present disclosure, various features of the present disclosure are sometimes grouped together into a single embodiment, drawing or the description thereof. However, the methods of the present disclosure should not be construed to represent the intent that the claimed scope of the present disclosure claims more features than those expressly recited in each claim. Rather, as represented in the corresponding claims, the point of the present disclosure may be that the corresponding technical problem can be solved with fewer features than all features of a single disclosed embodiment. Accordingly, the claims that follow the specific embodiment are hereby expressly incorporated into said specific embodiment, where each claim itself serves as a separate embodiment of the present disclosure.

Those skilled in the art will understand that, unless the features are mutually exclusive, any combination of the features disclosed in the present disclosure (including the claims, abstract and drawings) and the processes or units of any method or apparatus so disclosed may be used. Unless expressly stated otherwise, each feature disclosed in the present disclosure (including the claims, abstract and drawings) may be replaced by alternative feature that provide the same, equivalent or similar purpose.

Furthermore, those skilled in the art will understand that, although some embodiments described herein include certain features included in other embodiments but not other features, combinations of the features of different embodiments are intended to be within the scope of the present disclosure and form different embodiments. For example, in the claims, any one of the claimed embodiments may be used in any combination.

Various components of the present disclosure may be implemented in hardware, or in software module running on one or more processors, or in a combination thereof. Those skilled in the art will understand that a microprocessor or digital signal processor (DSP) may be used to implement some or all of the functions of some modules of the embodiments of the present disclosure. The present disclosure may also be implemented as a program (e.g., a computer program and a computer program product) for performing part or all of the methods described herein. Such program implementing the present disclosure may be stored on a computer-readable medium, or may have the form of one or more signals. Such signals may be downloaded from Internet sites, or be provided on carrier signals or in any other form.

It should be noted that the embodiments above intend to illustrate, but not limit the present disclosure, and that alternative embodiments may be made by those skilled in the art without departing from the scope of the appended claims. In the claims, no reference signs located between parentheses should be construed as limiting the claims. The present disclosure may be implemented by hardware including several different elements and by a suitably programmed computer. In unit claims enumerating multiple devices, several of these devices may be implemented by the same hardware. The words first, second, and third, etc. does not indicate any order. These words can be interpreted as names.

The description above is merely the specific embodiments of the present disclosure or the illustration of the specific embodiments, and the protection scope of the present disclosure will not be limited thereto. The changes or modifications made by any person skilled in the art within the technical scope disclosed in the present disclosure should be covered by the protection scope of the present disclosure. The protection scope of the present disclosure shall be determined by the claims.

What is claimed is:

1. A viscoelasticity measurement method comprising:

generating shear waves propagating in a target area of an object to be examined;

transmitting ultrasonic waves to the target area for tracking the shear waves, and receiving ultrasonic echoes returned from the target area to obtain ultrasonic echo data;

obtaining tissue motion information in propagation of the shear waves according to the ultrasonic echo data;

obtaining tissue motion target information corresponding to at least two shear waves of different frequencies from the tissue motion information; and outputting the tissue motion target information corresponding to the at least two shear waves of different frequencies, the tissue motion target information representing a viscosity characteristic of the target area, comprising:

generating and displaying a tissue motion image according to the tissue motion target information corresponding to the at least two shear waves of different frequencies, wherein one frame of the tissue motion image displays the tissue motion target information corresponding to the at least two shear waves of different frequencies at one or more preset times, wherein the displayed tissue motion target information comprises curves respectively representing propagation positions of the at least two shear waves of different frequencies in a depth direction and a width direction of the object; or one frame of the tissue motion image displays time information required for the at least two shear waves of different frequencies to propagate to at least one preset propagation position, wherein the displayed time information comprises curves respectively representing propagation positions of the at least two shear waves of different frequencies in the depth direction of the object with respect to time.

2. The viscoelasticity measurement method of claim 1, wherein outputting the tissue motion target information corresponding to the at least two shear waves of different frequencies further comprises:

outputting the tissue motion target information corresponding to the at least two shear waves of different frequencies in a numerical manner.

3. The viscoelasticity measurement method of claim 2, wherein outputting the tissue motion target information corresponding to the at least two shear waves of different frequencies in the numerical manner comprises:

generating a parameter representing the viscosity characteristic of the target area according to the tissue motion target information of the at least two shear waves of different frequencies, and displaying the parameter.

4. The viscoelasticity measurement method of claim 3, wherein the parameter comprises at least one of:

a distance between propagation positions of shear waves of different frequencies at a same time;

a ratio between a distance and a propagation distance of a shear wave of one of the different frequencies within a preset time; and a time difference between times required for shear waves of different frequencies to propagate to a same preset propagation position.

5. The viscoelasticity measurement method of claim 1, wherein, the tissue motion image comprises at least one frame of the tissue motion image, and each of the at least one frame of the tissue motion image displays the tissue motion target information corresponding to the at least two shear waves of different frequencies at a preset time.

6. The viscoelasticity measurement method of claim 5, wherein, when the tissue motion image comprises at least two frames of the tissue motion image, displaying the tissue motion image comprises dynamically displaying the at least two frames of the tissue motion image in chronological order or cumulatively display the at least two frames of the tissue motion image in chronological order.

7. The viscoelasticity measurement method of claim 5, wherein each of the at least one frame of the tissue motion image displays the tissue motion target information corresponding to the at least two shear waves of different frequencies at a preset time, and frames of target tissue motion images corresponding to the at least two shear waves of different frequencies at different times are displayed in a same window.

8. The viscoelasticity measurement method of claim 1, wherein intervals between the preset times are equal or unequal.

9. The viscoelasticity measurement method of claim 1, wherein the tissue motion target information corresponding to the at least two shear waves of different frequencies are displayed by at least one of a spectrum, a color, and a line.

10. The viscoelasticity measurement method of claim 1, wherein the tissue motion information comprises at least one of a tissue displacement, a tissue motion velocity, and a tissue acceleration.

11. The viscoelasticity measurement method of claim 1, wherein obtaining the tissue motion target information corresponding to the at least two shear waves of different frequencies from the tissue motion information comprises:

filtering the tissue motion information with at least two filters of different frequencies to obtain the tissue motion target information corresponding to the at least two shear waves of different frequencies respectively.

12. The viscoelasticity measurement method of claim 1, wherein displaying the tissue motion image further comprises:

one frame of the tissue motion image displays propagation positions of the at least two shear waves of different frequencies at a plurality of preset times.

13. The viscoelasticity measurement method of claim 1, wherein one frame of the tissue motion image displays the tissue motion target information corresponding to the at least two shear waves of different frequencies at one or more preset times in different spectrums, different colors, or different lines.

14. The viscoelasticity measurement method of claim 1, wherein one frame of the tissue motion image displays the time information required for the at least two shear waves of different frequencies to propagate to at least one preset propagation position in different spectrums, different colors, or different lines.

15. A viscoelasticity measurement method, comprising:

generating at least two shear waves of different frequencies sequentially in a target area of an object to be examined;

transmitting ultrasonic waves to the target area for tracking the at least two shear waves of different frequencies, and receiving ultrasonic echoes returned from the target area to obtain ultrasonic echo data;

obtaining tissue motion target information corresponding to the at least two shear waves of different frequencies according to the ultrasonic echo data; and outputting the tissue motion target information corresponding to the at least two shear waves of different frequencies, the tissue motion target information representing a viscosity characteristic of the target area, comprising:

generating and displaying a tissue motion image according to the tissue motion target information corresponding to the at least two shear waves of different frequencies, wherein one frame of the tissue motion image displays the tissue motion target information corresponding to the at least two shear waves of different frequencies at one or more preset times, wherein the displayed tissue motion target information comprises curves respectively representing propagation positions of the at least two shear waves of different frequencies in a depth direction and a width direction of the object; or one frame of the tissue motion image displays time information required for the at least two shear waves of different frequencies to propagate to at least one preset propagation position, wherein the displayed time information comprises curves respectively representing propagation positions of the at least two shear waves of different frequencies in the depth direction of the object with respect to time.

16. The viscoelasticity measurement method of claim 15, wherein outputting the tissue motion target information corresponding to the at least two shear waves of different frequencies further comprises:

outputting the tissue motion target information corresponding to the at least two shear waves of different frequencies in a numerical manner.

17. The viscoelasticity measurement method of claim 16, wherein outputting the tissue motion target information corresponding to the at least two shear waves of different frequencies in the numerical manner comprises:

generating a parameter representing the viscosity characteristic of the target area according to the tissue motion target information of the at least two shear waves of different frequencies, and displaying the parameter.

\* \* \* \* \*